United States Patent [19]

Högnelid et al.

[11] Patent Number: 5,782,889
[45] Date of Patent: Jul. 21, 1998

[54] CARDIAC STIMULATOR WITH ATRIAL CAPTURE VERIFICATION

[75] Inventors: Kurt Högnelid, Bromma; Per Frånberg, Stockholm, both of Sweden

[73] Assignee: Pacesetter AB, Solnal, Sweden

[21] Appl. No.: 789,394

[22] Filed: Jan. 29, 1997

[30] Foreign Application Priority Data

Jan. 29, 1996 [SE] Sweden .................. 9600310

[51] Int. Cl.⁶ .................................. A61N 1/365
[52] U.S. Cl. ................................................ 607/28
[58] Field of Search .......................... 607/9, 11, 25, 607/27, 28

[56] References Cited

U.S. PATENT DOCUMENTS

| | | |
|---|---|---|
| 4,686,988 | 8/1987 | Sholder . |
| 4,905,696 | 3/1990 | Amundson et al. . |
| 5,165,404 | 11/1992 | Andersson . |
| 5,443,485 | 8/1995 | Housworth et al. . |
| 5,476,786 | 12/1995 | Lu et al. .................. 607/28 |
| 5,601,615 | 2/1997 | Markowitz et al. ......... 607/28 |

*Primary Examiner*—William E. Kamm
*Assistant Examiner*—George R. Evanisko
*Attorney, Agent, or Firm*—Hill & Simpson

[57] ABSTRACT

A heart stimulator, with verification of capture in the atrium of a heart, contains an atrial pulse generator which, via an atrial electrode, emits stimulation pulses in the atrium and a ventricular detector which senses depolarization signals in the ventricle via a ventricular electrode. The time which elapses between two consecutive stimulation pulses emitted in the atrium can be varied, and variation in ventricular events associated with the stimulation pulses is studied. If the ventricular events vary in time in the same way stimulation pulses emitted in the atrium vary, AV conduction is functional, and capture is present in the atrium.

8 Claims, 1 Drawing Sheet

CARDIAC STIMULATOR WITH ATRIAL CAPTURE VERIFICATION

BACKGROUND OF THE INVENTION

1. Field of the Invention

The present invention is directed to a cardiac stimulator of the type wherein capture is verified, and in particular to such a cardiac stimulator wherein atrial capture is verified.

2. Description of the Prior Art

In heart stimulation, an electrical pulse, i.e. a heart stimulation pulse, is delivered to heart tissue in the atrium and/or ventricle for the purpose of inducing contraction of the atrium and/or the ventricle, thereby supporting the heart's pumping capacity. "Capture" refers to the depolarization of heart cells produced by a stimulation pulse. Depolarization (usually) results in the contraction of heart tissue. In a stimulation pulse, the lowest energy content needed to achieve depolarization of heart cells is usually referred to as the "stimulation threshold". The response of heart tissue to a stimulation pulse is referred to as "evoked response", (ER) which can be capture or non-capture.

AUTOCAPTURE™ refers to automatic control and setting of the stimulation threshold level. When this function is used for capture in the ventricle, the "stimulation threshold" can be defined as the lowest stimulation level for which at least two heart stimulation pulses result in capture. Checks on the stimulation threshold are performed at certain intervals.

From U.S. Pat. No. 5,165,404 a heart stimulator is known which contains means for determining the stimulation threshold of stimulation pulses. The description of the prior art in that patent indicates the way the stimulation threshold can be determined, by successive reduction in the energy content of stimulation pulses and study of the heart's response to each stimulation pulse. When the heart stops responding, the stimulation threshold is defined as the lowest stimulation pulse amplitude which evoked a heart response.

In identification of the stimulation threshold, the way in which the lowest level at which capture occurs by reducing the amplitude of the stimulation pulse was described above. Since the energy content of the stimulation pulse is decisive to the success of stimulation, the duration of the stimulation pulse is also important to successful stimulation. Identification of the stimulation threshold is performed using the prevailing programmed duration. Typical values for the duration of the stimulation pulse range from 0.03 to 1.0 ms.

The AUTOCAPTURE™ systems currently in use are for AUTOCAPTURE™ in the ventricle in which signal levels for evoked response are so high that they are easily detected and identified. Signals in the atrium, however, are much weaker, and emitted stimulation pulses interfere with measurements. This means that detection of evoked response must be performed in some other manner, so the autocapture used in the ventricle is not directly applicable in the atrium.

AUTOCAPTURE™ means that the level of stimulation voltage is periodically checked, making pacemaker operation more reliable. Another effect of AUTOCAPTURE™ is to minimize current consumption, thereby increasing the life of the pacemaker battery. Particularly in dual chamber pacemakers, i.e. DDD pacemakers, which stimulate and sense in both the ventricle and atrium, there is also a need for an AUTOCAPTURE™ function in the atrium in order to achieve more reliable stimulation and minimize current consumption.

DDD pacemakers can be used in patients with widely varying heart conditions. Some patients have intact conduction between the atrium and ventricle (AV conduction), and some do not. The mechanical pumping capability of the atrium also varies from patient to patient. The atrium in some patients does beat electrically, i.e. there is depolarization of the heart cells, but this depolarization fails to evoke any mechanical contraction of the atrium, i.e. the atrium lack a pumping capability.

U.S. Pat. No. 4,905,696 shows that an impedance signal measured in the ventricle undergoes a rapid, easily detected change in atrial contraction. Measurement is made between the tip of the electrode in the ventricle and the pacemaker's metal enclosure, or an indifferent electrode closer to the stimulation electrode, by means of a high-frequency signal applied to the electrode tip. When the atrium contracts, impedance in the ventricle drops as the ventricle fills with blood.

This causes a rapid, detectable change in the impedance signal. A review of the prior art in the aforementioned U.S. Pat. No. 4,905,696 also sets forth other ways of detecting atrial contraction which utilize an electrode in the atrium.

SUMMARY OF THE INVENTION

It is an object of the present invention to provide an implantable cardiac stimulator wherein capture, in particular atrial capture, is verified in a manner which is reliable and minimizes current consumption.

The above object is achieved in accordance with the principles of the present invention in an implantable cardiac stimulator having an atrial pulse generator which delivers atrial stimulation pulses to the atrium of a heart via at least one atrial electrode, a ventricular detector which senses depolarization signals in the ventricle via a ventricular electrode, a counter connected to the atrial pulse generator which varies and sets a first interval between successive stimulation pulses, and a comparison unit, connected to the ventricular detector, which sets a second interval between successive, sensed depolarization signals associated with the respective atrial stimulation pulses which compares the variation in at least one first interval with a variation in at least one second interval for determining the presence of capture in the atrium. Capture is determined to be present when the result of the comparison yields a value which is less than a predetermined minimum value.

In a version of the invention, variations in a predetermined number of first intervals can be compared with variations in a predetermined number of second intervals in order to determine the presence of capture.

Thus, in the heart stimulator according to the invention the time which elapses between two consecutively stimulation pulses emitted in the atrium is varied, and variations in ventricular events corresponding thereto are studied. This makes it possible to verify whether the patient's AV conduction is intact. If ventricular events vary in time in the same way the stimulator pulses emitted in the atrium vary, AV conduction and capture are present in the atrium.

In an embodiment of the heart stimulator according to the invention, the stimulator also contains an impedance meter for measuring impedance between the atrium and the ventricle, the impedance meter being arranged to measure impedance if the interval between consecutive ventricular depolarizations fails to vary in the same way as the interval between stimulation pulses in the atrium, capture being deemed to be present if impedance measurement shows the presence of an atrial contraction and no concomitant ventricular activity is detected in the ventricle's depolarization signal.

3

If, according to the invention, the absence of functional AV conduction has been verified in the patient, an examination must therefore be performed to ascertain whether atrial stimulation pulses delivered to the atrium cause atrial contraction, i.e. whether the patient has a functional atrium. This is investigated by studying the change in impedance between the atrial electrode and the ventricular electrode during atrial stimulation. To ensure that the change in impedance is caused by an atrial contraction and not by concomitant ventricular activity, the depolarization signal in the ventricle is studied to make sure no concomitant ventricular activity is present. Capture is present in the atrium if atrial contraction is verified in the aforementioned manner and no concomitant ventricular activity is found.

If the measured impedance value indicates that no atrial contraction is present, despite the use of maximal stimulation energy, the atrium is non-functional, and the heart stimulator, according to another embodiment of the invention, automatically switches to a stimulation mode which only stimulates the ventricle, e.g. VVI or VVI-R. Verification of capture in the atrium is a function which can be constantly activated or which is only activated at a specific interval, e.g. once an hour.

DESCRIPTION OF THE PREFERRED EMBODIMENTS

Figure 1:
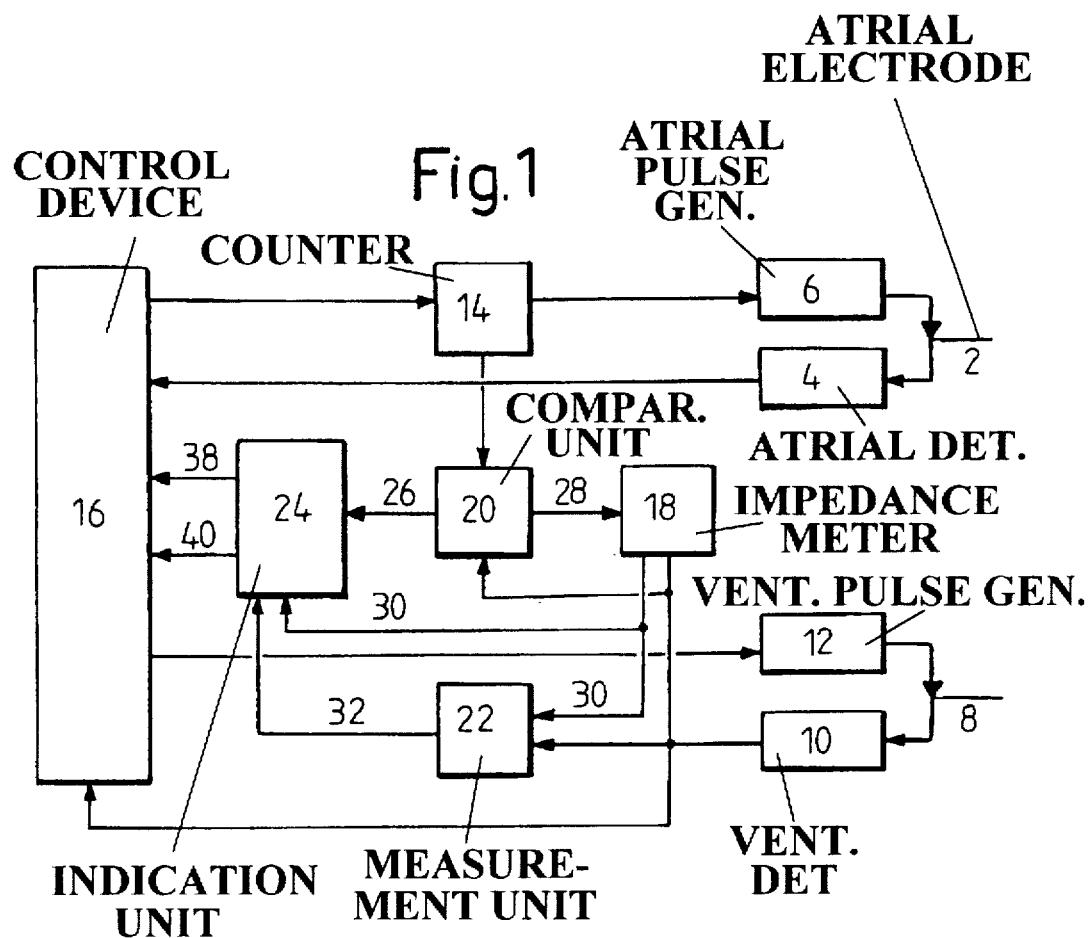
FIG. 1 is a block diagram of a heart stimulator according to the invention.

FIG. 1 shows a block diagram of a heart stimulator having an atrial electrode 2, an atrial detector 4, an atrial pulse generator 6, a ventricular electrode 8, a ventricular detector 10 and a ventricular pulse generator 12. The atrial detector 4 is connected, via a counter 14, to a programmable control device 16 to which the atrial pulse generator 6, the ventricular detector 10 and the ventricular pulse generator 12 are connected. The ventricular detector 10 is also connected to an impedance meter 18, a comparison unit 20 and a measurement unit 22. An indication unit 24 is connected to the impedance meter 18, the comparison unit 20 and the measurement unit 22. The indication unit 24 is also connected to the programmable control device 16. The atrial detector 2 is able to sense depolarization signals in the atrium, and the atrial pulse generator 4 is able, via the atrial electrode 2, to deliver stimulation pulses to the atrium. The ventricular detector 10 is able to sense depolarization signals in the ventricle, and the ventricular pulse generator 12 is able, via the ventricular electrode 8, to deliver stimulation pulses to the ventricle.

The programmable control device 16 can communicate with a programmer (not shown) outside the body by means of telemetry (radio signals). Various parameters for the heart stimulator's operation, such as the heart stimulator's operating mode (e.g. VVI, DDD), the frequency at which capture is to be checked, etc., can be set with the programmer. The reprogramming of the heart stimulator with the aid of a programmer is familiar to those skilled in the art and therefore need not be described herein.

In stimulation of the atrium, the control device 16 causes the atrial pulse generator 6 to emit a stimulation pulse with a preset energy content to the heart. This control is exercised via the counter 14, which can vary a first interval between consecutively emitted stimulation pulses by shortening or

4 lengthening the interval by a predetermined period of time, this time being brief in relation to the interval between consecutively emitted stimulation pulses in the atrium. This predetermined period of time, with which the first interval is shortened or lengthened, is on the order of 10–100 ms. The counter 14 sends information identifying the duration of the first interval to the comparison unit 20.

The ventricular detector 10 senses the heart's depolarization signal in the ventricle. This signal is sent to e.g. the comparison unit 20 which measures the time between consecutive QRS complexes, associated with the atrial stimulation pulses, in the depolarization signal, thus constituting a second interval. The comparison unit 20 also compares the first interval with the second interval. A high degree of measurement reliability is attained when each of a predetermined number of consecutive first intervals is varied and compared to each of a predetermined number of second intervals respectively associated with the first time intervals.

Comparison between the first interval and the second interval, or between the first interval and second interval, can be performed e.g. by determining the difference between the time intervals. If the difference is less than a predetermined minimum value, the intervals are deemed to be equal.

If the time between QRS complexes varies in the same way as the time between stimulation pulses emitted in the atrium, electrical conduction between the atrium and ventricle (AV conduction) is intact, and capture is then present in the atrium. If, in this manner, capture is found to be present in the atrium, a first signal 26 will go "high". This signal is sent to the indication unit 24. The first signal 26 is "low" in the normal state. If the time between QRS complexes does not vary in the same way the time between atrial stimulation pulses varies, i.e. if the difference between intervals exceeds the predetermined minimum value, a second signal 28 will go "high", this signal being sent to the impedance meter 18. The second signal 28 is normally "low".

The impedance meter 18, which is connected to the ventricular detector measures, if the second signal 28 received from the comparison unit 20 is "high", impedance between the electrode in the atrium and the electrode in the ventricle during atrial stimulation. In atrial contraction, there is an easily detectable change in impedance which is utilized by the impedance meter 18 for detecting atrial contraction. Impedance measurement can be performed in a number of ways familiar to those skilled in the art, e.g. as shown in above-cited U.S. Pat. No. 4,905,696.

If impedance measurement has shown that atrial contraction is present, a third signal 30 goes "high". This signal is emitted by the impedance meter 18 and sent to the indication unit 24 and the measurement unit 22. The normal state of the third signal 30 is "low", but the signal goes "high" for a given period of time when atrial contraction is detected.

Thus, the third signal 30 is sent to the measurement unit 22 to which a detected depolarization signal from the ventricular detector 10 is also sent. If the third signal 30 is "high" and the depolarization signal does not indicate simultaneous ventricular activity, a fourth signal 32 goes "high". This fourth signal 32 is sent to the indication unit 24. The fourth signal 32 thus goes "high" if impedance measurement shows that atrial contraction is present and no simultaneous ventricular activity is detected. Generation of the fourth signal 32 verifies the presence of capture in the atrium.

The first signal 26, third signal 30 and fourth signal 32 are sent to (the indication unit 24.

Figure 2:
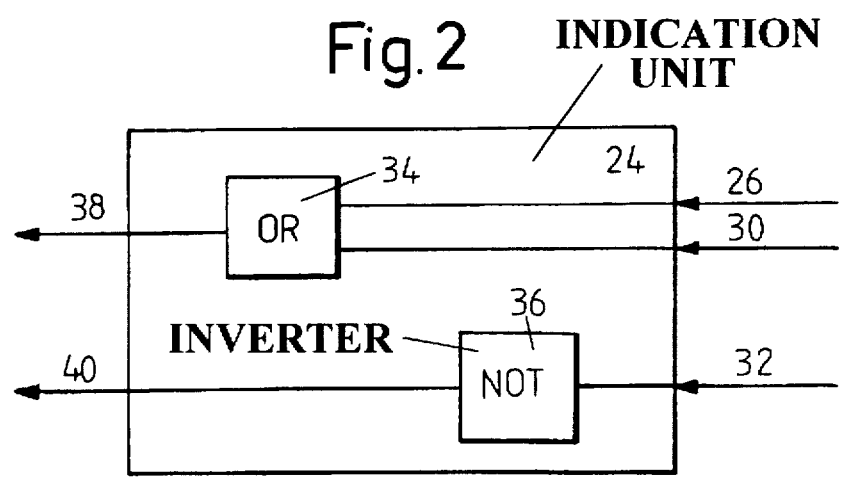
FIG. 2 is a block diagram of an indication means according to the invention.

FIG. 2 shows a block diagram of the indication unit 24 formed by an OR gate 34 and an inverter gate 36. The first signal 26 and the third signal 30 are sent to the OR gate 34. If either the first signal 26 or the third signal 30 is "high", the OR gate emits a first indication signal 38 which is "high", indicating the presence of capture in the atrium. The fourth signal 32 is sent to the inverter gate 36. If the fourth signal 32 is "low" for a predetermined period of time (because no atrial contraction at a predetermined point in time occured), the inverter gate 36 emits an output signal which is the inverse of the fourth signal 32 serving as the input signal. This output signal of the inverter gate 36 constitutes a second indication signal 40, which is "high" at the predetermined point in time, and indicates that no atrial contraction is occurring and no capture is accordingly present in the atrium. The predetermined point in time, which determines when the second indication signal 40 is relevant, depends on when impedance measurement is performed and this depends, in turn, on the time during which the atrium is stimulated. When the programmable control device 16 creates a time window after each emitted atrial stimulation pulse, if the second signal 28 is "high", and the second indication signal 40 is studied during this time window, a "high" state for the second indication signal 40 can easily be identified.

If the second indication signal is "high", this means that no atrial contraction is occurring, and thus the atrium lacks any pumping capability, and the heart stimulator can accordingly switch to a stimulation mode in which the atrium is not stimulated, e.g. VVI or VVI-R.

The check on the presence of atrial capture can be performed after every atrial stimulation or at every second or third atrial stimulation. Another option is to perform the check at a given interval, e.g. once an hour.

The stimulation threshold can be checked when capture is detected in the atrium. Such a check can be made at given intervals, e.g. 1, 2, 4 or 8 hours. By definition, the stimulation threshold is the lowest level of stimulation at which at least two consecutive stimulation pulses result in capture. When the stimulation threshold is checked, the prevailing level of stimulation is the starting point, and this level is gradually reduced by a predetermined amount. If capture is still present (at least two consecutive captures), the level is again reduced by the predetermined amount etc. until no capture is detected. The new stimulation threshold is identified as the lowest level at which capture is present, and the new stimulation level is obtained by adding a safety margin to an identified stimulation threshold.

Known means (not shown) for performing a check on the level of stimulation are arranged inside the programmable control device 16.

The above-described method for checking the level of stimulation in the atrium works the same way as the check on the level of stimulation in the ventricle, a well-known technique for those skilled in the art, and need not be described here.

The atrial electrode 2 and the ventricular electrode 8 can be arranged on individual electrode leads placed in the atrium and ventricle respectively or arranged on the same electrode lead, which then serves as a single lead.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:
    an atrial pulse generator which emits a plurality of stimulation pulses;
    at least one atrial electrode connected to said atrial pulse generator and adapted for in vivo implantation in an atrium of a heart for delivering said stimulation pulses to said atrium;
    a ventricular electrode adapted for in vivo implantation in a ventricle of said heart;
    a ventricular detector, connected to said ventricular electrode, which senses depolarization signals in the ventricle of said heart, each stimulation pulse being followed by a depolarization signal;
    counter means, connected to said atrial pulse generator, for varying and setting a first interval between successive stimulation pulses; and
    comparison means, connected to said ventricular detector, for identifying a second interval between successive depolarization signals sensed by said ventricular detector, and for comparing a variation in at least one first interval with a variation in at least one second interval and generating a signal indicating atrial capture if a result of said comparison has a value less than a predetermined minimum value.

2. A heart stimulator as claimed in claim 1 wherein said comparison means comprises means for comparing variations in a predetermined number of first intervals with variations in a predetermined number of second intervals.

3. A heart stimulator as claimed in claim 1 further comprising:
    an atrial detector, connected to said at least one atrial electrode, which senses depolarization signals in the atrium via said atrial electrode;
    a ventricular pulse generator connected to said ventricular electrode which emits ventricular stimulation pulses supplied to the ventricle via said ventricular electrode; and
    impedance measuring means, connected to said comparison means, for measuring impedance between the atrium and the ventricle if said result of said comparison is less than said predetermined minimum value, for generating a signal which additionally verifies atrial capture if a measured impedance exhibits a level indicating an atrial contraction has occurred and said ventricular detector senses no ventricular activity in the depolarization signal from the ventricle.

4. A heart stimulator as claimed in claim 3 wherein said comparison means comprises means for emitting a "high" signal if said variation in said at least one second interval is equal to said variation in said at least one first interval, as a first signal indicating atrial capture, and for setting a second signal to a "high" value and for sending said second signal to said means for measuring impedance if said variation in said at least one first interval is not equal to said variation in said at least one second interval.

5. A heart stimulator as claimed in claim 4 wherein said impedance measuring means comprises means for setting a third signal to a "high" level if said measured impedance exhibits said level indicating an atrial contraction, and further comprising measurement means, connected to said ventricular detector and to said impedance measuring means, for setting a fourth signal to a "high" level when said third signal is "high" if said ventricular detector senses no ventricular activity in said depolarization signal at the same time as an atrial contraction.

6. A heart stimulator as claimed in claim 5 further comprising indicator means, supplied with said first, third and fourth signals, for setting a first indication signal identifying a presence of capture in the atrium to a "high" level if either said first or fourth signals is at said "high" level.

7. A heart stimulator as claimed in claim 6 wherein said indication means comprises means for setting a second indication signal to a "high" level indicating that no atrial contraction is present if said measured impedance value indicates that no atrial contraction is present, and control means, supplied with said first and second indication signals, for controlling said atrial pulse generator and said ventricular pulse generator in a VVI mode.

8. A heart stimulator as claimed in claim 1 wherein each atrial stimulation pulse has an energy content, and further comprising means for automatically successively reducing said energy content of said stimulation pulses when atrial capture is present for identifying a stimulation threshold of the atrium for setting an energy content for subsequent stimulation pulses having a lowest stimulation energy required to produce atrial capture.

* * * * *